United States Patent
Zhao et al.

(10) Patent No.: US 11,639,331 B2
(45) Date of Patent: May 2, 2023

(54) TRANS, TRANS-DIKETONE OXIME ESTER ISOMER, MANUFACTURING METHOD THEREOF AND APPLICATION THEREOF

(71) Applicant: INSIGHT HIGH TECHNOLOGY CO., LTD, Beijing (CN)

(72) Inventors: Wenchao Zhao, Beijing (CN); Jiaqi Li, Beijing (CN); Chenlong Wang, Beijing (CN)

(73) Assignee: INSIGHT HIGH TECHNOLOGY CO., LTD, Beijing (CN)

( * ) Notice: Subject to any disclaimer, the term of this patent is extended or adjusted under 35 U.S.C. 154(b) by 388 days.

(21) Appl. No.: 16/756,477

(22) PCT Filed: Aug. 30, 2018

(86) PCT No.: PCT/CN2018/103202
§ 371 (c)(1),
(2) Date: Apr. 16, 2020

(87) PCT Pub. No.: WO2019/076145
PCT Pub. Date: Apr. 25, 2019

(65) Prior Publication Data
US 2021/0198193 A1 Jul. 1, 2021

(30) Foreign Application Priority Data
Oct. 16, 2017 (CN) .................. 201710958349.X

(51) Int. Cl.
| | | |
|---|---|---|
| *C07C 323/22* | (2006.01) | |
| *C07C 319/20* | (2006.01) | |
| *C08F 2/48* | (2006.01) | |
| *C09D 4/00* | (2006.01) | |
| *C09D 11/101* | (2014.01) | |
| *C09J 4/00* | (2006.01) | |
| *C09J 11/06* | (2006.01) | |
| *G02B 5/22* | (2006.01) | |
| *G03F 7/00* | (2006.01) | |
| *G03F 7/031* | (2006.01) | |

(52) U.S. Cl.
CPC .......... *C07C 323/22* (2013.01); *C07C 319/20* (2013.01); *C08F 2/48* (2013.01); *C09D 4/00* (2013.01); *C09D 11/101* (2013.01); *C09J 4/00* (2013.01); *C09J 11/06* (2013.01); *G02B 5/223* (2013.01); *G03F 7/0007* (2013.01); *G03F 7/031* (2013.01)

(58) Field of Classification Search
CPC ......................................................... C08F 2/48
See application file for complete search history.

(56) References Cited

U.S. PATENT DOCUMENTS

2016/0376226 A1* 12/2016 Qian .................... C07D 409/14
548/441

FOREIGN PATENT DOCUMENTS

| | | | | |
|---|---|---|---|---|
| CN | 1514845 | A | 7/2004 | |
| CN | 101941920 | A | 1/2011 | |
| CN | 102015633 | A | 4/2011 | |
| CN | 102492059 | A | 6/2012 | |
| CN | 103833872 | A * | 6/2014 | ........... C07C 249/04 |
| CN | 103833872 | A | 6/2014 | |
| CN | 104076606 | A | 10/2014 | |
| CN | 104910053 | A | 9/2015 | |
| CN | 105504105 | A | 4/2016 | |
| CN | 105523975 | A | 4/2016 | |
| JP | 2011105713 | A | 6/2011 | |
| JP | 2015093842 | A | 5/2015 | |
| JP | 2016167030 | A | 9/2016 | |
| JP | 2016196437 | A | 11/2016 | |
| JP | 2017512886 | A | 5/2017 | |
| JP | 2017523465 | A | 8/2017 | |
| WO | WO-2015027833 | A1 * | 3/2015 | ........... C07D 209/86 |
| WO | 2016192611 | A1 | 12/2016 | |

OTHER PUBLICATIONS

Anonymous, Use of Ketoxime-Esters, Research Disclosure, Sep. 30, 2000, RD437035, pp. 1-4 (Year: 2000).*
Anonymous, Use of Ketoxime-Esters, Research Disclosure, Sep. 10, 2000, RD437035, Abstract (Year: 2000).*

* cited by examiner

*Primary Examiner* — Chanceity N Robinson
(74) *Attorney, Agent, or Firm* — Yu Gang

(57) ABSTRACT

A diketone oxime ester compound shown in formula I and a manufacturing method therefor, and a photo-curable composition using the compound of formula I as a photoinitiator. The composition has extremely high light sensitivity and relatively low yellowing resistance when applied to prepare a color filter for a light resistance device such as a display screen.

5 Claims, No Drawings

TRANS, TRANS-DIKETONE OXIME ESTER ISOMER, MANUFACTURING METHOD THEREOF AND APPLICATION THEREOF

TECHNICAL FIELD

The present disclosure relates to the technical field of photoinitiators, in particular to a diketone oxime ester compound which is characterized in that two esterified oxime groups in the molecule are in the α-position of the carbonyl.

BACKGROUND

Oxime ester compounds have been discovered as photoinitiators for a long time, and U.S. Pat. Nos. 3,558,309 and 4,255,513 both disclose oxime ester compounds as photoinitiators: however, oxime esters of some structures have poor thermal stability or low photosensitivity and are difficult to meet the use requirements of the modern electronics industry in regard to thermal stability, photosensitivity, etc. CN1241562A and CN1514845A disclose a series of oxime ester compounds, and two varieties OXEO1 and OXEO2 are available in the market. Products with similar properties are oxime esters 305 and 304 disclosed in CN10165472B and CN101508744B.

OXE01

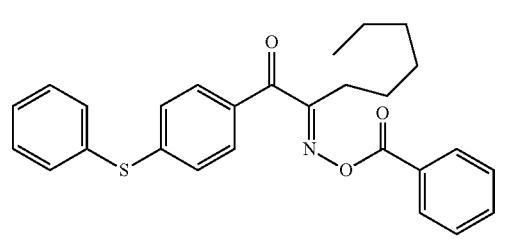

OXE02

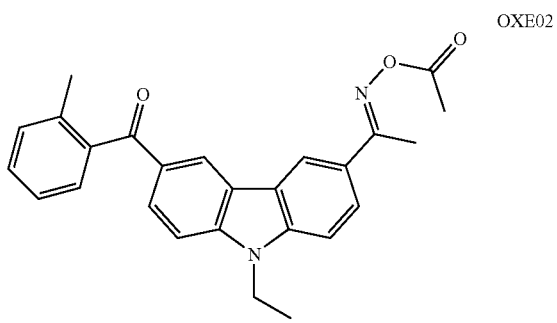

305

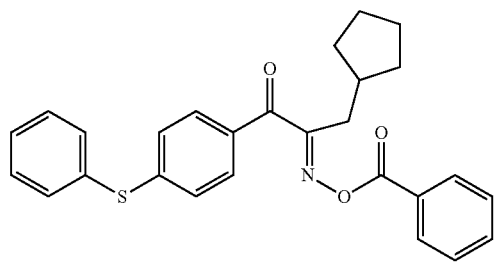

304

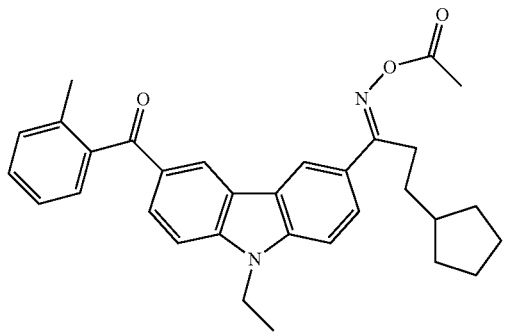

In color photoresists, more and more attention has been paid to the effect of color difference caused by the yellowing of photoinitiator, and searching for new active compounds with both high sensitivity and low yellowing becomes the focus of technical research in the industry. Even a slight decrease of yellowing is regarded as a significant progress in technology by users. The various bisoxime ester derivatives disclosed in the patent WO2008138732 taking phenylcarbazole as a precursor have two oxime ester groups in one molecule, and experiments prove that the yellowing property of carbazole oxime ester cannot meet the color difference requirement of color photoresists.

The increase in sensitivity predicts that less photoinitiator can be used to achieve a same cure effect, with difference in sensitivity being 1.4 times the difference in each step in the evaluation of sensitivity using a 21-step gray scale gradient, which is also considered a significant improvement by the user. Therefore, obtaining high-sensitivity compounds as photoinitiators has always been the focus of attention of those skilled in the art.

The specification of patent CN 1514845A discloses certain diketone oxime esters synthesized on the basis of diphenyl sulfide. For example, the example 38 is an oil, which is unfavorable for production and manufacture and difficult to obtain high-purity products, while the quality requirements by users in the field on the photoinitiator materials such as purity, chroma, metal ions and the like are high; example 39 is a solid; and the specification of the patent CN 103833872 A discloses a compound 1, a compound 3 and a compound 4 thereof.

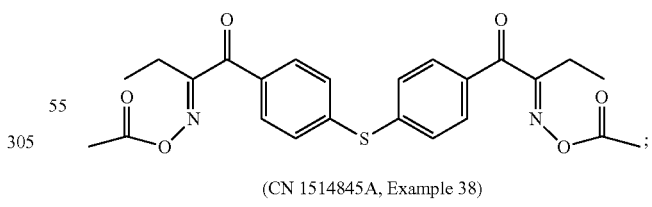

(CN 1514845A, Example 38)

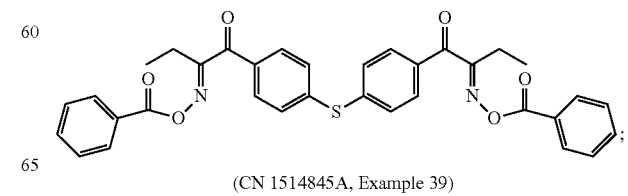

(CN 1514845A, Example 39)

-continued

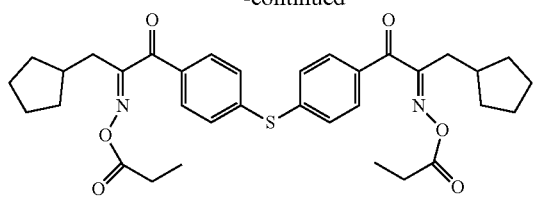

(CN 103833872 A, Compound 1)

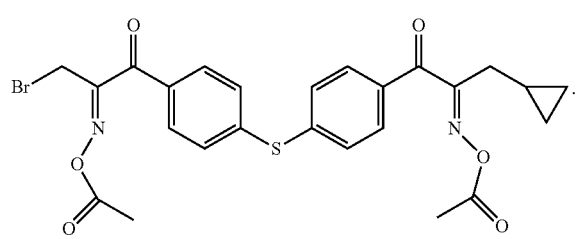

(CN 103833872 A, Compound 3)

SUMMARY

In the experiments, the present inventor surprisingly found that a solid diketone oxime ester with trans, trans-isomerism, i.e. a compound of formula I, as a photoinitiator, has significantly high sensitivity and relatively low yellowing, and is suitable for red, green and blue colored photoresists or colorless transparent photoresists.

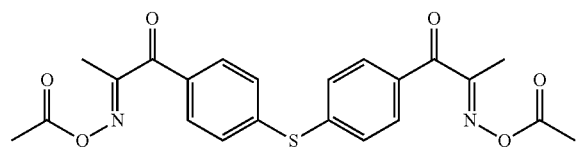
(I)

The present disclosure also provides a preparation method of the compound of formula I, which is characterized by comprising the following steps:

Step 1: carrying out dipropionylation on a diphenyl sulfide to obtain a compound of formula II;

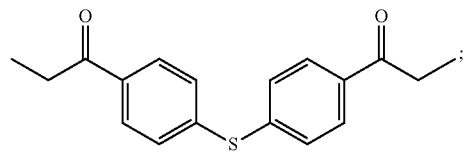
(II)

(2) Step 2: carrying out selective oximation, a method comprising subjecting the compound of the formula II and an alkyl nitrite to an oxime reaction of the carbonyl ortho carbon atoms in an acidic solution to obtain a corresponding trans, trans-isomeric diketone oxime intermediate compound of formula III

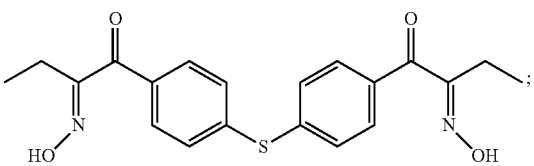
(III)

and (3) Step 3: carrying out esterification reaction on the intermediate compound of formula III and an acetic anhydride or an acetyl chloride to obtain the compound of formula I which is a trans, trans isomer;

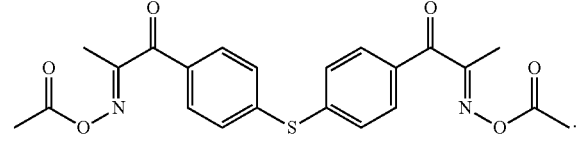
(I)

The present disclosure also provides a photo-curable composition which comprises (a) a photoinitiator and (b) at least one free-radically polymerizable carbon-carbon double bond compound, wherein the (a) photoinitiator must and at least comprises the compound of the formula I.

The photoinitiator (a) may further comprise, in addition to the above compound of formula I, other commercially available photoinitiators as an co-initiator component (c).

The photo-curable composition further contains other additives (d), such as a developable resin, a pigment, a defoamer and other necessary functional component.

The photoinitiator (a) accounts for 0.05-15% preferably from 1-10%, by weight of the total cured composition; and the remaining components account for the remaining percentages other than the above components.

Component (b), the free-radically polymerizable carbon-carbon double bond compound, is a photo-curable monomer, and the molecule of the photo-curable monomer comprises one carbon-carbon double bond or two or more carbon-carbon double bonds. A compound comprising one carbon-carbon double bond is preferably an acrylate compound, a methacrylate compound, for example an acrylate or methacrylate of a monohydric alcohol: methyl acrylate, butyl acrylate, 2-ethylhexyl acrylate, cyclohexyl acrylate, isobornyl acrylate, hydroxyethyl acrylate, methyl methacrylate and acrylonitrile, N, N-dialkyl acrylamide, N-vinyl pyrrolidone, vinyl benzene, vinyl acetate, and vinyl ether.

Examples of a compound comprising two or more carbon-carbon double bonds are acrylates or methacrylates of alkyl diols and polyols, or acrylates of polyester polyols, polyether polyols, epoxy polyols, polyurethane, polyols, vinyl ethers and unsaturated polyesters of unsaturated dicarboxylic polyols, such as polyethylene glycol diacrylate, neopentyl glycol diacrylate, trimethylolpropane triacrylate, polyethoxylated trimethylolpropane triacrylate, pentaerythritol tetraacrylate, dipentaerythritol hexaacrylate, polyester oligomer acrylate, polyurethane oligomer acrylate, aromatic epoxy acrylate, and ethylene glycol maleate polyester.

Not only can these carbon-carbon double bond compounds be used alone, but also more than two can be used in combination or pre-copolymerized between mixtures to form oligomers for use in preparation of the composition. When the polymeric monomer contains an alkali-soluble group such as a carboxylic acid group, a polymer resin having alkali solubility is obtained, which can be used to prepare a photoresist or an aqueous dispersion emulsion.

In addition to the compound of general structural formula I serving as a photoinitiator, other type of commercially available photoinitiator or synergist can be compounded to serve as a co-initiator component (c) according to the requirements of the application of the composition, and is usually another oxime ester compound: Omnirad 1312 from IGM Co., ltd; Irgature OXE01, Irgature OXE02, Irgature OXE03, Irgature OXE04 from BASF, TR-PBG-305, TR-PBG-3057, TR-PBG-304 from Changzhou Tronly New Electronic Materials Co., ltd, NCI930, N11919, NCI831 from Adeka Co., ltd, TMP-P07 from Takoma Co., ltd, SPI-03 from Samyang Co., ltd; or α-hydroxyketone compounds such as 2-hydroxy-2-methyl-1-phenylpropanone, 1-hydroxycyclohexylbenzophenone; α-aminoketones such as 2-methyl-2-morpholinyl-(4-methylthiophenyl)-1-propanone, 2-dimethylamino-2-benzyl-(4-morpholinophenyl)-1-butanone; 2, 2-diethoxy-1, 2-diacetophenone; methyl benzoyl formate, diethylene glycol bisbenzoyl formate, polybutanediol bisbenzoyl formate; (2, 4, 6-trimethylbenzoyl) diphenylphosphine oxide, bis (2, 4, 6-trimethylbenzoyl) phenylphosphine oxide; benzophenone and substituted derivatives thereof such as benzophenone, 4-methylbenzophenone, 4-chlorobenzophenone, 4-phenylbenzophenone, 2'-chloro-4-phenylbenzophenone, 4-methylthiobenzophenone, 4-(2-hydroxyethylthio) benzophenone, 4-hydroxybenzophenone laurate, benzophenone-4-oxoacetic acid polyethylene glycol ester; thioxanthone and substituted derivatives thereof such as 2-isopropylthioxanthone, 2, 4-diethylthioxanthone, 1-chloro-4-propoxythiaxanthone, polyethylene glycol thioxanthone-2-formate, polyethylene glycol thioxanthone-2-oxoacetate; halomethyltriazines such as 2-(4-methoxyphenyl)-4, 6-bis (trichloromethyl)-[1, 3, 5]-triazine; hexaarylbiimidazole such as hexa-o-chlorophenyl diimidazole; ferrocene compound; titanocene compound; coumarin; camphorquinone; acridine such as 9-phenylacridine; amine such as 4, 4'-bis (diethylamino) benzophenone, ethyl 4-dimethylaminobenzoate, triethanolamine, methyldiethanolamine or active amine compound such as diethylamine and ethoxylated trimethylolpropane triacrylate adduct; phosphite such as triphenyl phosphite, trilauryl phosphite; and a chain transfer agent such as hexanedithiol, octanethiol.

Component (d) comprises a pigment, dye. Pigments are essential components for the printing ink and for the preparation of the optical filter and can be, as required, red (C. I. Pigment Red 177), green, blue, black, white, yellow, magenta, cyan and other special colors, respectively, corresponding pigments being such as carbon black, phthalocyanine blue (phthalocyanine C. I. Pigment Blue 15: 3), C. I. Pigment Green 7, titanium dioxide and other commercial varieties. The pigment concentration generally accounts for 10-40% by weight of all solid components of the composition.

Component (d) also includes the necessary additives: a phenolic and hindered amine inhibitor such as p-methoxyphenol, nitrosophenylhydroxylamine aluminum complex inhibitor; a light absorber such as 2-(2'-hydroxyphenyl)-benzotriazoles, salicylates, triazines; a leveling agent such as vinyltriethoxysilane; a wetting agent, and a dispersing agent. They are used in amounts limited by the property indexes of the composition without particularly requirements.

Component (d) further comprises a developable resin. Wherein for an alkali-soluble developable resin, for example a polyacrylate copolymer containing carboxylic acid side chains, the comonomer may be selected from acrylic or methacrylic acid, alkyl acrylates, alkyl methacrylates, styrene, oligostyrene; examples of solvent-developable resins comprise cellulose ester and cellulose ether, polyvinyl acetate, polyvinyl butyrals, polystyrene, polycarbonate, polyvinyl chloride, polyester, and polyimide resins of conventional varieties. When the developable resin is an alkali soluble resin, the composition can be used in photoresist and in the production of color filters in display devices.

The composition further comprises a thermosetting resin and a photocurable resin component (e), such as a cellulose solution, polyisocyanate, and polyimide, which are suitable for the flow requirement of the photo-curing, heat-curing staging process.

At least one compound having an epoxy group is also allowed to be added to the composition as thermosetting component (f) as well as an epoxy-based curing accelerator (g). The compound having an epoxy group as thermosetting component (f) may be a well-known thermosetting epoxy compound such as an aliphatic epoxy resin or an aromatic epoxy resin, preferably a bisphenol S type epoxy resin such as BPS-200 produced by Japan Chemical Company, a bisphenol A type epoxy resin, a novolak type epoxy resin, and the like, and partial esters thereof. The amount of the component (f) used in the composition is 30-70 parts relative to 100 parts by weight of component (b).

When the component (f) is used, the accelerator (g) is optionally used as a synergistic component to provide a good cure promoting effect, and examples comprise amine accelerators, imidazole accelerators and other commonly used epoxy resin hardeners, in amounts not exceeding 5% by weight of the component (f).

In addition to the components (a), (b), (c), (d), (e), (f), and (g) described above, other additives (h) commonly used in the art may also be used in the composition, including: one of the additives for improving the adhesiveness, film-forming hardness and the like of the composition, e.g. an inorganic filler, such as barium sulfate, powdered silicon dioxide, talcum powder, calcium carbonate, mica powder and the like, in an amount within 30% of the total weight of the composition;

The compositions can also be used after dilution with a solvent according to the requirements of the field of application, and the suitable solvent is selected from: ketones such as methyl ethyl ketone, and cyclohexanone; hydrocarbons such as toluene, xylene, octane, petroleum ether, and naphtha; alcohols such as n-butanol, propylene glycol and the like; alcohol ethers and esters thereof, such as propylene glycol monomethyl ether, diethylene glycol monomethyl ether, propylene glycol monomethyl ether acetate, methyl 3-methoxypropionate, and the like; and amides such as N, N-dimethylformamide.

The composition or the mixture diluted by the solvent is prepared according to the production method of the ink, and protected from light.

The use of the composition is for manufacture of one of the following colored or transparent articles: coatings, adhesives or inks, and photoresists, and the articles in turn are used for printing, 3D printing, production of color filters in display devices, image reproduction technology, printed circuit board dielectric layers, electronic device packaging, optical switches, three-dimensional molds, quartz fiber protective layers and medical products.

The present disclosure provides a method for curing a carbon-carbon double bond compound in the photo-curable composition, namely, the composition is coated on a substrate, and the coating layer is cured by irradiating 190-600 nm light. The light comes from a high pressure mercury lamp or LED lamp. The composition can be irradiated with light waves in the range of 190-600 nm or light waves of which the output light wavelength is controlled by a grating, or the coating layer of the composition can be irradiated and cured with an LED light source of any certain wavelength range between 360 nm and 410 nm, such as a 365 nm LED light source. The LED is defined as a light emitting semiconductor diode.

The method for manufacturing a relief pattern by the photo-curable composition is: firstly diluting the photo-curable composition with a solvent; and then coating the diluted photo-curable composition on a substrate, and removing the unexposed part by drying, exposing and developing to obtain the relief pattern.

The composition containing the compound of the formula I, the monomer, the alkali-soluble resin, the pigment and the additive can be used as photoresist, with high photosensitivity, easy to develop by an alkali aqueous solution, no swelling and deformation, clear in imaging effect, and suitable for preparing etching photoresist and solder resist photoresist; and it is used for displaying image and recording materials; for an inkjet ink cured by an LED lamp; it is used in the production process of LCDs, OLEDs and PDPs, also in the manufacture of various printing plates and the production process of electronic circuit plates or integrated circuits, as well as for forming isolation coatings for various electronic components.

The composition has excellent oxygen inhibition resistance and heat processing resistance, meeting production process requirements of color filters, and it is particularly suitable for production of liquid crystal displays and organic semiconductor electroluminescent displays.

The composition provided by the present disclosure, as a photoresist, contains a proper solvent according to needs, and is sequentially subjected to coating, drying, exposure, development and heat treatment processes to form black, and red, green and blue three-color pixel patterns to obtain a complete color filter. The substrates of these color filters may be glass or organic polymer films and ceramic sheets.

The composition is coated on a flat plate or curved surface substrate, and dried to obtain a film layer; and the unexposed part is removed through mask exposure and development method to obtain the relief image. The color filter containing black, red, green and blue pixels is obtained through coating, exposure, development and heat treatment processes from the composition consisting of the compound of the formula I, the photo-curable monomer, the alkali-soluble resin, the pigment and the additive. Necessary processes such as cleaning is also comprised.

The composition of the present disclosure is uniformly applied to the substrate to be coated using a coating technique commonly used in the art such as spin coating, roll coating, spray coating, transfer printing and the like, and the coating amount is determined as required, with a typical thickness being 0.1 to 10 microns. When the composition contains a solvent component, the solvent is volatilized by a heating process, such as a 100° C. drying process, while the non-volatile component remains on the substrate and forms an adhesive layer, with the most common adhesive layer thickness being 1-2 microns.

The next step is exposure, if the UV laser is not used for direct exposure, the mask with the image is placed on the adhesive layer, and the ultraviolet or visible light source emits light with a certain range of wavelengths so as to set energy to penetrate through the transparent part of the mask for exposure, and thus the light receiving part of the adhesive layer is cured, and the shielded part is not cured.

Next is development, wherein the unexposed part is removed to obtain a relief pattern. The development process is operated with parameters well known to those skilled in the art, such as dispense at 30° C. and rinse. The development is usually carried out using an aqueous alkaline solution, for example, an aqueous solution of hydroxide and carbonate of an alkali metal, and aqueous ammonia. A quantitative wetting agent such as a surfactant, an organic solvent such as cyclohexanone, acetone, 2-ethoxyethanol and the like may also be added to the aqueous solution if necessary. The development manner in which the exposed film is immersed in the developer bath or the developer is sprayed onto the exposed film is possible, and the specific development temperature and time depend on the development effect. The alkaline solution for development is an aqueous solution in which an alkaline substance such as sodium hydroxide, potassium hydroxide, sodium carbonate, potassium carbonate, sodium hydrogen carbonate, potassium hydrogen carbonate, triethanolamine, morpholine, trisodium phosphate is dissolved in water or an aqueous solution containing a water-soluble organic solvent at a concentration of 0.01-10% by weight; the above aqueous solution may also be added with a surfactant at a concentration of 0.01-1% by weight.

The final heat treatment process can optimize the image fastness, typically by baking in a 200-260° C. oven for 15-45 minutes, typically at 230° C. for 30 minutes.

Based on the production process of the known color filter, the color filter device can be manufactured by using the composition, which has excellent processing performance, clear array and high light transmittance and is used for producing a high-quality display.

The photo-curable composition is not only used for manufacturing color photoresists, but also can be used for black photoresists (BM), PCB dry films, photo-curable inks, LED-curable inks and 3D printing inks.

Effect of the Disclosure

The compound of formula I has remarkable high sensitivity and low yellowing property when used as a photoinitiator in a red, green and blue color photoresist formula.

DETAILED DESCRIPTION

The present disclosure can be illustrated in more detail from the examples, and all consumptions are based on weight, unless otherwise specified.

Embodiment 1 Synthesis

Synthesis of 4,4'-Dipropionyldiphenyl Sulfide (Compound of Formula II)

79.0 G (0.424 mol) of diphenyl sulfide was weighed, dissolved in 600 g of 1,2-dichloroethane, and added with 124.4 g (0.933 mol) of anhydrous aluminum trichloride, followed by stirring and cooling to 0° C.; the temperature was kept below 5° C., 82.4 g (0.891 mol) of propionyl chloride was added dropwise, the addition was completed after 2 h, and stirring was continued at 0° C. for 2 h; the reaction solution was added dropwise into 450 ml of 10% diluted hydrochloric acid of which the temperature was controlled to be not higher than 30° C., stirring was continued for 1 h after adding, and the lower organic phase was separated; the organic phase was washed with 300 ml of water for three times in sequence, and subjected to reduced pressure distillation to recover the solvent to give 126 g of a residue; 240 ml of n-hexane was added while hot, and the temperature was kept to clarify the solution; natural cooling was carried out to enable it to crystallize, and when the solution temperature was lower than 30° C., the crystal bottle was put into an ice-water bath to continuously cool to 0° C.; suction filtration was carried out gave a white filter cake, which was dried under reduced pressure at 50° C. to give 117.6 g of white crystals with a yield of 93%, purity of 98.5% by HPLC analysis, and melting range of 123.1-130.3° C. $^1$H-NMR data indicated that the product was 4,4'-dipropionyldiphenyl sulfide.

Synthesis of Trans, Trans-Isomeric Diketone Oxime (Compounds of Formula III)

30 G (0.1 mol) of 4,4'-dipropionyl diphenyl sulfide obtained from 1-1 was weighted, dissolved by 100 g of dimethyl sulfoxide, and added with 3.0 g of 36% concentrated hydrochloric acid; the temperature was kept on a water bath of 20-25° C. and the mixture was stirred, added dropwise with 25 g (0.24 mol) of n-butyl nitrite within 30 min, and stirred for 10 h; the reaction liquid was added dropwise into 1 L of ice water to separate a light yellow solid, followed by suction filtration, and drying under reduced pressure, 27 g of a product was obtained with a purity of 97.80% by an HPLC analysis, yield of 75%, and melting range of 162.8-169.5° C. $^1$H-NMR data indicated that the product was a trans, trans-isomeric diketone oxime compound of formula III. $^1$H-NMR (CDCl$_3$), δ(ppm) value data: 2.022 (s, 6H, 2CH$_3$), 7.425/7.452 (d, 4H, 4ArH), 7.823/7.851 (d, 4H, 4ArH), 12.450 (s, 2H, 2NOH).

Synthesis of Trans, Trans-Isomeric Diketone Oxime Ester (Compounds of Formula I)

In a reaction bottle, 24.5 g (0.068 mol) of a 1-2 product trans, trans-isomeric diketoximide (the compound of formula III) and 150 ml of toluene was added; the reaction bottle was put into a water bath of 20-25° C.; 19.6 g (0.19 mol) of acetic anhydride was added dropwise into the reaction bottle through a constant pressure dropping funnel, and stirred for 6 h; 100 ml of water was added into the reaction solution, and stirred for 30 min; the toluene phase was washed with 100 ml of 1% sodium bicarbonate solution, 50 ml of water and 50 ml of water sequentially, and toluene solution was filtered, distilled under reduced pressure to recover toluene to obtain 28.5 g of a crude yellow solid; 55 ml of hot ethyl acetate was added to dissolve the solid, and supplemented with 85 ml of hot n-hexane, naturally cooled to precipitate crystals; followed by suction filtration, and the filter cake was dried under vacuum to obtain 27.2 g of a light yellow solid crystal product with a content of 99.2% by the HPLC analysis, yield of 90.8%; and melting range of 108.0-111.5° C.; $^1$H-NMR (CDCl$_3$), δ (ppm) value data: 2.274 (s, 6H, 2CH$_3$), 2.293 (s, 6H, 2COCH$_3$), 7.417/7.445 (d, 4H, 4ArH), 8.050/8.078 (d, 4H, 4ArH).

Embodiment 2 Preparation of Alkali Soluble Resin

180 G of benzyl methacrylate, 60 g of methacrylic acid, 60 g of hydroxyethyl methacrylate, 15 g of azobisisobutyronitrile, 6 g of dodecyl mercaptan and 1000 ml of toluene were uniformly mixed, and put into a constant-pressure dropping funnel; 1000 ml of toluene was put into a three-neck flask which was then installed with a stirring device, the constant-pressure dropping funnel and a thermometer, and after starting stirring, gas in the flask was replaced with nitrogen; the flask was heat to enable the temperature of the solvent to reach 80-85° C. and keep warm, the monomer mixed solution was started to add dropwise for about 1 h; the reaction was continued for 6 h; followed by cooling naturally, stirring was stopped to allow the resin to settle, the upper clear solution was sucked, and the lower resin containing the solvent was filtered; the resin filter cake was eluted with 500 ml of toluene, and dried under reduced pressure to obtain 250 g of white powdery solid resin, which was dissolved in 1000 g of PMA (propylene glycol methyl ether acetate) as a 20% solution for later use.

Embodiment 3 Preparation and Development of Photoresists

All the components were prepared into the photo-curable composition according to the ink preparation method based on the weight ratio of the formulations 3A, 3B, 3C and 3D in Table 1, and the photo-curable composition was in a fluid liquid state.

Each of the above liquid compositions was coated on a glass surface using a line bar method, and baked for 3 minutes at 80° C. to evaporate off the solvent PMA, and the residual film thickness was measured to be 2 microns for later use.

First Group Exposure Tests

A 21-step gray gradient scale was placed on the film, 2000 W high-pressure mercury lamp light was filtered through a 365 nm grating filter, and the distance between the film and the grating was 10 cm to make the exposure amount reach 200 mJ/cm$^2$.

Followed by immersion in a 1% sodium carbonate solution bath of 30° C. for 1 minute, the maximum step of film retention that could be displayed was recorded, the greater the number, the greater the photosensitivity of the composition measured, the higher the photo-cure rate and film-forming property of the photoresist, and the results are shown in Table 2.

Second Group Yellowness Test

Another standby coating film was taken, 2000 W high-pressure mercury lamp light was filtered through a 365 nm grating filter, and the distance between the film and the grating was 10 cm to make the exposure amount reach 200 mJ/cm$^2$.

The exposed films were heated in a 230° C. oven for 30 min and the films were tested for yellowness indexes on a yellowness apparatus and the results are shown in Table 2.

TABLE 1

| Composition raw material proportioning | | | | | |
|---|---|---|---|---|---|
| | 3A | 3B | 3C | 3D | Sources |
| Compound of Embodiment 1 | 5 | | | | |
| Comparative Compound 1 | | 5 | | | Commercial product OXE01 |
| Comparative Compound 2 | | | 5 | | Prepared according to Embodiment 39 of patent CN 1514845A |
| Comparative Compound 3 | | | | 5 | Prepared according to Embodiment 1 of patent CN 103833872A |
| Alkali soluble resin solution | 500 | 500 | 500 | 500 | Embodiment 2 |
| Dipentaerythritol hexaacrylate | 100 | 100 | 100 | 100 | Allnex Co., Ltd |

TABLE 2

| | Test Results | | | |
|---|---|---|---|---|
| | 3A | 3B | 3C | 3D |
| Maximum film retention step | 13 | 10 | 11 | 11 |
| yellowness index (Yi D) | 1.05 | 1.15 | 1.35 | 1.34 |

The results in Table 2 show that the exposure sensitivity of the 3A photoresist prepared using the compound of Embodiment 1 is significantly better than that of the photocurable composition prepared using the control compound, increasing the sensitivity of the photoresist; the 3A photoresist formulated with the compound of Embodiment 1 has the lowest yellowness index.

Embodiment 4

Filter Film Preparation from Photoresist and Exposure Development

The formula included the following components: 500 parts of an alkali-soluble resin solution (Embodiment 2), 100 parts of dipentaerythritol hexaacrylate (Cytec), 8 parts of a photoinitiator and 50 parts of a red pigment L3920 (BASF). The ink was uniformly ground according to an ink preparation method, and four kinds of 4A-4D inks were obtained due to different initiators.

For the coating step, each of the above liquid compositions was coated on a glass surface using a line bar method, and baked for 3 minutes at 80° C. to evaporate off the solvent PMA, and the residual film thickness was measured to be 2 microns; a pattern mask with a transparent line width of 100 microns was covered; and 2000 W high-pressure mercury lamp light was filtered through a 365 nm grating filter, and the distance between the film and the grating was 10 cm to make the exposure amount reach 80 mJ/cm$^2$.

The development was carried out for BP+10S with 1% aqueous sodium hydroxide solution, followed by rinsing with deionized water, and drying at 100° C., and the line width value CD after development was measured, and the experimental results are shown in Table 3. BP refers to the film breaking point during development.

TABLE 3

| | Red photoresist exposure evaluation | | | |
| --- | --- | --- | --- | --- |
| | Ink number | | | |
| Photoinitiator sample | 4A Compound of formula I | 4B Control Compound 1 | 4C Control Compound 2 | 4D Control Compound 3 |
| BP(s) | 34 | 35 | 38 | 37 |
| CD(μm) | 105 | 96 | 99 | 100 |

As can be seen from Table 3, the ink 4A containing the compound of the present disclosure exhibits the best exposure sensitivity as judged by the Critical Dimension CD, i.e., the compound of the present disclosure is significantly more sensitive than all of the control compounds 1, 2, 3.

What is claimed is:

1. A process for producing a relief pattern, comprising diluting a photo-curable composition with a solvent, coating the photo-curable composition on a substrate, drying off the solvent to obtain a coated layer, curing the coated layer by irradiating with light having a wavelength of 190-600 nm, and removing unexposed part by exposure and development methods;

the photo-curable composition includes a compound of formula I as a photoinitiator, at least one free-radically polymerizable carbon-carbon double bond compound and optionally other components, the compound of formula I in which both oxime groups are trans form,

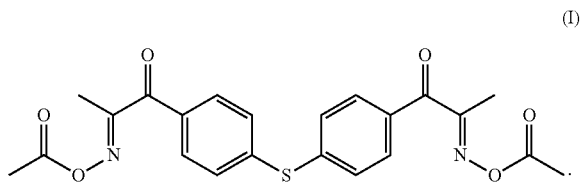 [SMILES: CC(=O)O/N=C(\C)C(=O)c1ccc(Sc2ccc(C(=O)/C(C)=N/OC(C)=O)cc2)cc1]

(I)

2. The process for producing the relief pattern of claim 1, wherein the photoinitiator accounts for 0.05-15% by weight of the total composition, and the at least one carbon-carbon double bond compound and other components account for the remaining percentages other than the above components.

3. The process for producing the relief pattern of claim 1, wherein the at least one carbon-carbon double bond compound is selected from acrylate compounds and methacrylate compounds.

4. The process for producing the relief pattern of claim 1, wherein further comprising an additive.

5. The process for producing the relief pattern of claim 4, wherein the additive comprises a developable resin, a pigment or a dye.

* * * * *